US00PP14541P29

(12) United States Plant Patent
Bottoms et al.

(10) Patent No.: US PP14,541 P2
(45) Date of Patent: Feb. 17, 2004

(54) SCHEFFLERA PLANT NAMED 'PVN III'

(50) Latin Name: *Schefflera arboricola*
Varietal Denomination: PVN III

(76) Inventors: Ellsworth D. Bottoms, 2518 Haas Rd., Apopka, FL (US) 32712; Luseane Bottoms, 2518 Haas Rd., Apopka, FL (US) 32712

( * ) Notice: Subject to any disclaimer, the term of this patent is extended or adjusted under 35 U.S.C. 154(b) by 0 days.

(21) Appl. No.: 10/313,114

(22) Filed: Dec. 6, 2002

(51) Int. Cl.[7] ..... A01H 5/00
(52) U.S. Cl. ..... Plt./377
(58) Field of Search ..... Plt./377

*Primary Examiner*—Bruce R. Campell
*Assistant Examiner*—Annette H. Para
(74) *Attorney, Agent, or Firm*—C. A. Whealy

(57) ABSTRACT

A distinct cultivar of Schefflera plant named 'PVN III', characterized by its compact, upright, outwardly spreading and mounded plant habit; short internodes and freely branching habit; dense and bushy growth habit; glossy dark green and creamy white variegated leaves.

1 Drawing Sheet

Botanical classification/cultivar designation: *Schefflera arboricola* cultivar PVN III.

BACKGROUND OF THE INVENTION

The present Invention relates to a new and distinct cultivar of Schefflera plant, botanically known as *Schefflera arboricola*, and hereinafter referred to by the cultivar name 'PVN III'.

The new Schefflera was discovered on Mar. 21, 1996 by the Inventors in a controlled environment in Apopka, Fla., as a naturally-occurring branch mutation of the *Schefflera arboricola* cultivar PVN I, disclosed in U.S. Plant Pat. No. 9,955. The cultivar PVN III was selected by the Inventors on the basis of its unique foliage variegation.

Asexual reproduction of the new cultivar by cuttings taken in Apopka, Fla., since Mar. 21, 1996, has shown that the unique features of this new Schefflera are stable and reproduced true to type in successive generations.

SUMMARY OF THE INVENTION

Plants of the cultivar PVN III have not been observed under all possible environmental conditions. The phenotype may vary somewhat with variations in environment and culture such as temperature and light intensity without, however, any variance in genotype.

The following traits have been repeatedly observed and are determined to be the unique characteristics of 'PVN III'. These characteristics in combination distinguish 'PVN III' as a new and distinct cultivar:

1. Compact, upright, outwardly spreading and mounded plant habit.
2. Short internodes and freely branching habit; dense and bushy growth habit.
3. Glossy dark green and creamy white variegated leaves.

Plants of the new Schefflera are similar to plants of the parent, the cultivar PVN I, in plant and growth habit, however plants of the new Schefflera differ primarily from plants of the cultivar PVN I in foliage coloration as plants of the cultivar PVN I have solid green-colored leaves.

Plants of the new Schefflera can be compared to plants of the cultivar PVN II Variegated, disclosed in U.S. Plant Pat. No. 10,831. However, in side-by-side comparisons conducted by the Inventors in Apopka, Fla., plants of the new Schefflera differed from plants of the cultivar PVN II Variegated in the following characteristics:

1. Plants of the new Schefflera had flatter leaves than plants of the cultivar PVN II Variegated.
2. Plants of the new Schefflera had dark green and creamy white variegated foliage whereas plants of the cultivar PVN II had green and yellow green variegated foliage.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

Colors in the photographs may differ slightly from the color values cited in the detailed botanical description which accurately describe the colors of the new Schefflera.

The photograph at the top of the sheet comprises a side perspective view of a typical container of 'PVN III' with four plants per container.

The photograph at the bottom of the sheet comprises a close-up view of typical leaves of 'PVN III'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and the following description were grown with four plants per container and in a polypropylene-covered shadehouse in Apopka, Fla., that provided a 60% reduction of the ambient light level. During the production of the plants, day temperatures ranged from 35 to 95° F. and night temperatures ranged from 35 to 70° F. Plants were about three years old when the description was taken.

Botanical classification: *Schefflera arboricola* cultivar PVN III.

Parentage: Naturally-occurring branch mutation of *Schefflera arboricola* cultivar PVN I, disclosed in U.S. Plant Pat. No. 9,955.

Propagation:

*Type.*—By cuttings.

*Time to initiate roots, summer.*—About 25 days at 70 to 90° F.

*Time to initiate roots, winter.*—About 52 to 59 days at 40 to 70° F.

*Time to develop roots, summer.*—About 30 days at 70 to 90° F.

*Time to develop roots, winter.*—About 65 to 72 days at 40 to 70° F.

*Root description.*—Numerous, dense, freely-branching; fibrous; white in color.

Plant description:

*Form.*—Compact, upright, outwardly spreading and mounded plant habit; inverted triangle; symmetrical. Freely basal branching; about seven lateral branches develop per plant after pinching.

*Plant height.*—About 42 cm.

*Plant diameter.*—About 72 cm.

*Vigor.*—Moderately vigorous.

*Lateral branches.*—Length: About 38 cm. Diameter: About 8 mm. Internode length: About 7.5 mm. Aspect: About 30 to 45° from upright. Strength: Flexible, but strong. Texture: Smooth, pubescent. Color: More green than 146A to 147A.

*Foliage description.*—Arrangement/appearance: Alternate; palmately compound with about seven leaflets per leaf; glossy. Leaflet length: About 5.2 cm. Leaflet width: About 2 cm. Leaflet shape: Oblanceolate. Leaflet apex: Acute, rounded. Leaflet base: Attenuate. Leaflet margin: Entire. Leaflet texture, upper and lower surfaces: Smooth, glabrous; leathery. Leaflet aspect: Mostly flat. Leaflet color: Young foliage, upper surface: Random central green area, close to 146A; random marginal greenish white areas, close to 154D. Leaflets may also be solid green, close to 146A. Young foliage, lower surface: Random central green area, close to 146B; random marginal greenish white areas, close to 154D. Leaflets may also be solid green, close to 146B. Mature foliage, upper surface: Random central dark green area, darker than 147A; random marginal creamy white areas, close to 158A. Leaflets may also be solid dark green, darker than 147A. Mature foliage, lower surface: Random central green area, closest to 147B; random marginal creamy white areas, close to 158A. Leaflets may also be solid green, closest to 147B. Veins, upper surface: Close to 147A. Veins, lower surface: Close to 146A. Leaflet petiole length: About 1.1 cm. Leaflet petiole diameter: About 1 mm. Leaflet petiole texture, upper and lower surfaces: Smooth, glabrous. Leaflet petiole color, upper and lower surfaces: Close to 146A. Leaf petiole length: About 6.3 cm. Leaf petiole diameter: About 2 mm. Leaf petiole texture, upper and lower surfaces: Smooth, glabrous. Leaf petiole color, upper and lower surfaces: Close to 146A.

Flower description: Flower development has not been observed on plants of the new Schefflera.

Disease/pest resistance: Plants of the new Schefflera have not been noted to be resistant to pathogens and pests common to Schefflera.

Weather tolerance: Plants of the new Schefflera have been observed to be tolerant to rain, wind and temperatures ranging from 35 to more than 100° F.

It is claimed:

1. A new and distinct cultivar of Schefflera plant named 'PVN III', as illustrated and described.

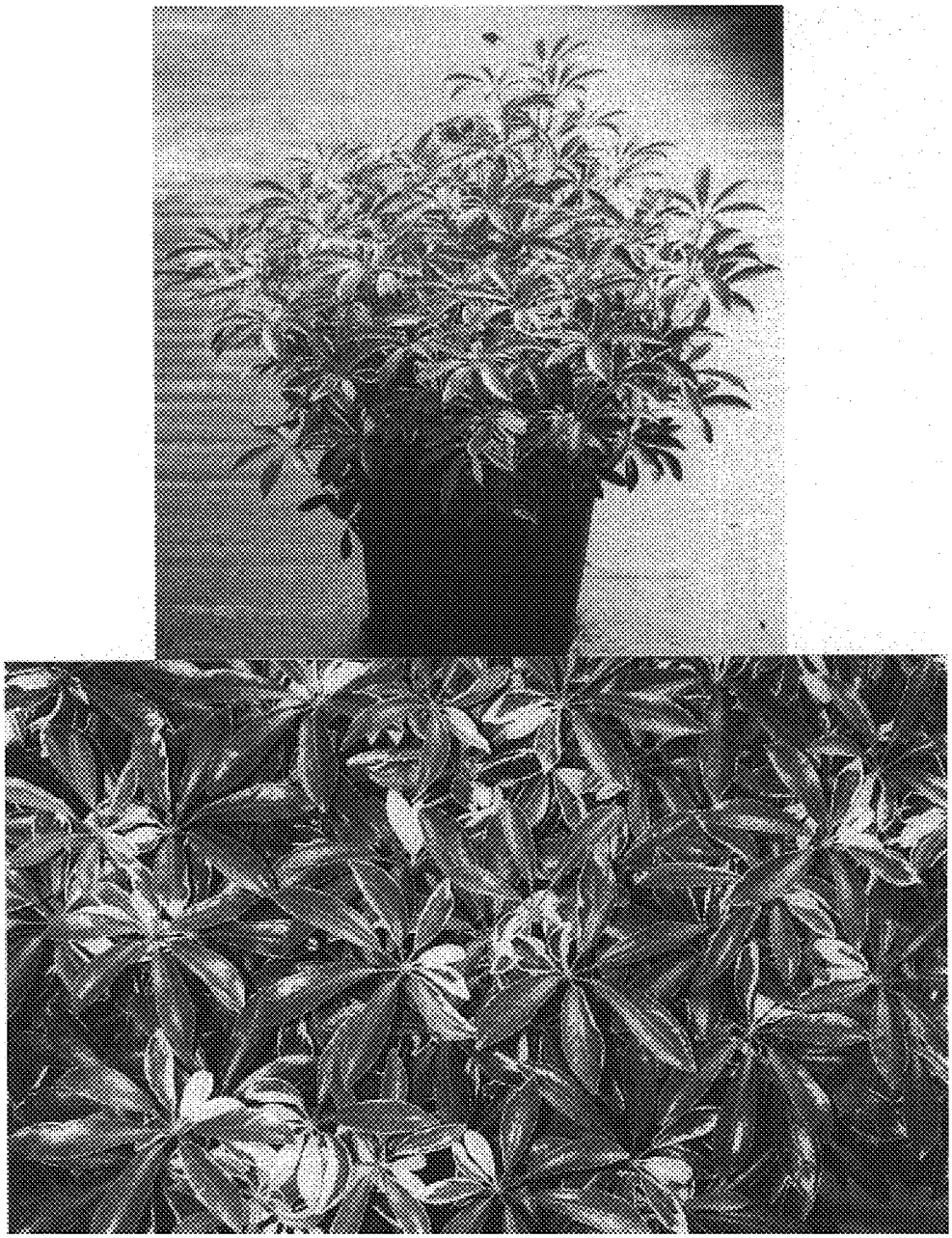

* * * * *